Nov. 21, 1944. A. C. GILLANDERS ET AL Re. 22,565

HOLDER AND DISPENSER FOR ROLLED SHEET MATERIAL

Original Filed Feb. 19, 1940

INVENTORS
ALEXANDER C. GILLANDERS
HARRY H. DAGGETT

BY Harold W. Spattingly
ATTORNEY.

Reissued Nov. 21, 1944 Re. 22,565

UNITED STATES PATENT OFFICE 22,565

HOLDER AND DISPENSER FOR ROLLED SHEET MATERIAL

Alexander C. Gillanders, West Hollywood, and Harry H. Daggett, Los Angeles, Calif., assignors to Johnson & Johnson, New Brunswick, N. J., a corporation of New Jersey Original No. 2,295,648, dated September 15, 1942, Serial No. 319,578, February 19, 1940. Application for reissue September 10, 1943, Serial No. 501,836

12 Claims. (Cl. 242—55.5)

Our invention relates to a dispenser for rolled sheet material and has particular reference to a holder and dispenser for surgical adhesive tape.

Adhesive tape of the type commonly employed by physicians and surgeons for securing surgical dressings in place ordinarily comprises a cloth backing upon which is placed a very adhesive layer such as the well known zinc oxide preparations. This tape is usually supplied to physicians, surgeons, hospitals and the like in the form of long sheets which are rolled upon a cardboard or paper cylinder.

Considerable difficulty is experienced in removing the desired amount of such tape since the adhesive coating on the one side of the tape adheres very strongly to the next lower layer upon which it is wound so that it is very difficult to unroll from the roll of tape the desired amount of such material. Furthermore, the cloth backing employed is usually a very strong material so that it is very difficult to tear from the roll the desired amount of material, recourse being had to scissors or similar shearing devices for separating from the roll of material the desired length which has been unrolled therefrom. Difficulty is also experienced as a result of the tendency of the adhesive material to adhere to the scissors or shears so that the cutting off operation is made very difficult. Considerable difficulty is also experienced in keeping such rolls of adhesive tape free from dust, dirt, and the like since it is common practice to leave these rolls lying on instrument tables and the like in order that they may be ready at hand.

It is accordingly an object of our invention to provide a holder for rolled sheet material in which means is provided for cutting the sheet when any desired length has been removed from the roll.

It is also an object of our invention to provide a holder and dispenser of the character set forth in the preceding paragraph which includes an enclosure for enclosing the roll of sheet material to exclude dust and dirt therefrom and which also includes a readily openable cover to give access to the rolled material.

It is a still further object of our invention to provide a holder and dispenser of the character set forth in the preceding paragraphs which is particularly designed for use with surgical adhesive tape which includes a cutter for cutting off any desired length of tape which has been removed from the roll, together with a means for holding the cut end of the material to permit ready removal from the roll of the next desired quantity.

It is a still further object of our invention to provide a device of the character set forth hereinbefore which is neat and attractive in appearance and which may be manufactured at a low cost.

Other objects and advantages of our invention will be apparent from a study of the following specifications, read in connection with the accompanying drawing, wherein.

Figure 1:
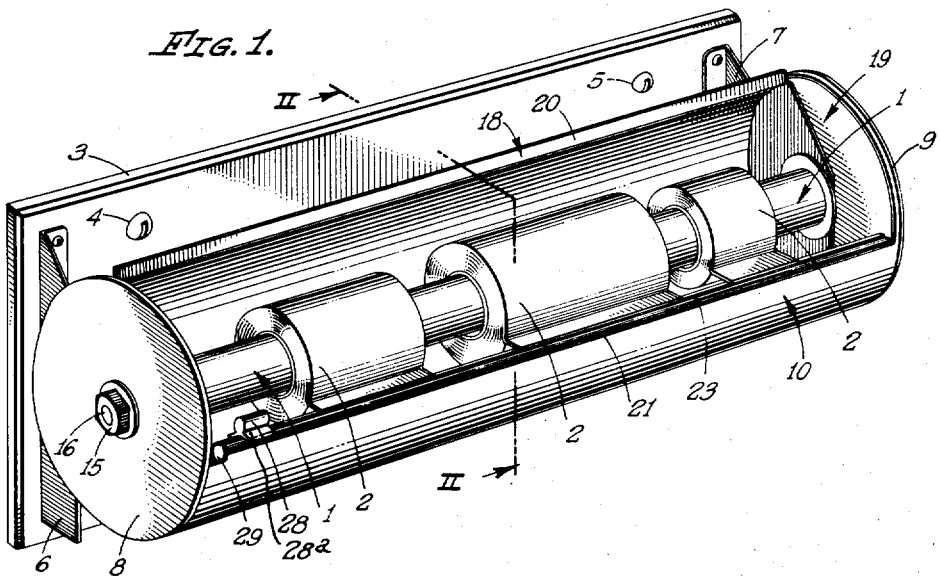
Fig. 1 is a perspective view of one form of holder and dispenser of our invention shown with the cover in the open position.

Referring to the drawing, we have illustrated in Fig. 1 the preferred embodiment of our invention as including a supporting member or rod 1 upon which may be supported, as by sliding thereover, rolls 2 of sheet material, such as adhesive tape. The rod 1 may be supported in any desired position by employing bracket members engaged with the opposite ends of the rod 1. In the form of the device illustrated herein, we employ also a mounting base 3 provided with apertures 4 and 5 permitting the use of screws or similar attaching means for securing the device to a wall or other supporting surface, the base 3 constituting a support for bracket members 6 and 7 which may also have circular portions 8 and 9 forming end closures for a housing 10, the housing 10 perferably having a cylindrical shape concentrically disposed relative to the rod 1.

Figure 4:
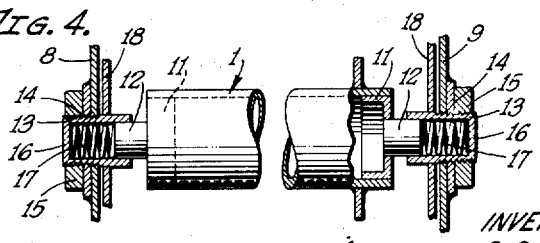
Fig. 4 is a fragmentary view with parts shown in section to illustrate the details of construction employed in the mounting of the material supporting roller.
Figure 5:
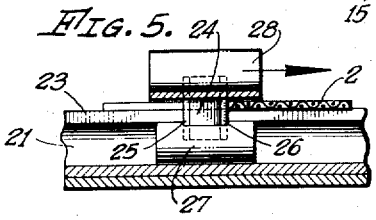
Fig. 5 is an enlarged fragmentary section taken substantially along the line V—V of Fig. 3 showing the details of construction of the cutter portion of our invention.

The supporting rod 1 is preferably in the form of a light weight metal tubing as indicated in Fig. 4 and is made readily removable from the housing 10 to permit the threading thereon of the rolls 2 of adhesive tape by employing a construction such as that illustrated in Fig. 4. As shown therein opposite ends of the tubing 1 are fitted with plugs or closures 11 to which is affixed, as by soldering or welding, short spindle members 12. These members are adapted to be received within a bore formed in a sleeve 13, the sleeve member 13 being secured to the bracket members 6 and 7 as by means of threads 14 and locked in place by lock nuts 15.

Each of the sleeve members 13 is preferably closed at its outer end as indicated at 16 and a compression spring 17 interposed between this end and the end of the spindle members 12. This construction permits the tubing 1 to be forced to one side against the pressure of one of the springs 17 a sufficient distance to bring the opposite spindle member 12 out of the sleeve within which it is received so as to permit the end thus freed to be moved out of alignment with the sleeve and the entire assembly removed from the housing.

Figure 2:
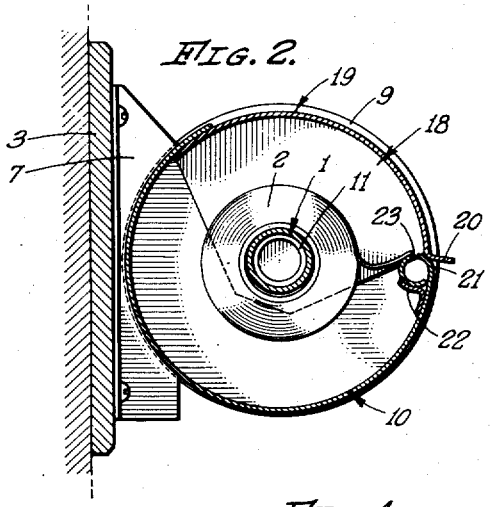
Fig. 2 is a cross sectional view taken substantially along the line II—II of Fig. 1 showing the relative positions of parts with the cover in the closed position.
Figure 3:
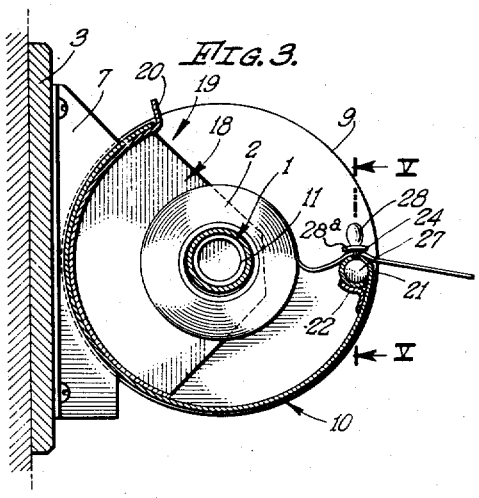
Fig. 3 is a cross sectional view similar to Fig. 2 but showing the cover in the open position and the manner in which the cutter is mounted to effect a cutting of material removed from the roll.

The housing 10 is also preferably fitted with a readily openable closure member 18 which may comprise a partially cylindrical section having sufficient arcuate length to enclose an open side 19 of the housing 10. Opposite ends of the closure 18 are provided with radial flange members which are in turn bored to receive the sleeves 13 so that the closure 18 may be moved in a pivotal fashion about the center of the housing 10 from an open position such as illustrated in Figs. 1 and 3 to a closed position such as that illustrated in Fig. 2. Ready opening and closing of this closure member may be facilitated by bending a portion 20 thereof outwardly from the surface of its cylindrical shape to provide a handle portion.

Inasmuch as some sheet materials, such as surgical adhesive tape, must be cut in order to separate an unrolled portion from the body of rolled material, we prefer to provide a means for readily cutting off such a removed portion. For this purpose we employ a cutter supporting bar or rail 21 which is also carried by the brackets 6 and 7 and disposed substantially parallel to the rod 1. In the form of device shown herein, the rail 21 comprises a rolled edge which extends along one longitudinal edge of the opening 19. This rolled edge may be constructed along the lines indicated in Figs. 2 and 3 wherein the edge of the material of the housing 10 is shown bent inwardly and back upon itself to provide a substantially cylindrical bead extending full length of the edge 21.

Between the under surface of this bead and the inner surface of the housing 10 we provide an angle supporting member 22 which is securely attached to the body portion of the housing 10 and to the under surface of the bead as by welding or soldering. The upper surface of the edge or bead 21 is then slit for its full length to provide a slot or kerf 23 in which may be received a cutter or knife 24. The cutter or knife is preferably disposed in a vertical plane and provided with front and rear cutting edges 25 and 26. This knife is adapted to be moved along the length of the slot 23, it being guided in such movement by a substantially cylindrical guiding member 27 received within the bore formed by the rolled bead 21. A handle 28 may be securely affixed to the upper protruding end of the cutter blade 24 so that the blade may be easily slid along the slot 23 from one end of the housing to the other, the handle 28 is preferably formed with laterally extending wings 28*a*, the under surfaces of which are curved to lie close to the upper surface of the bead 21. These wings 28*a* serve to prevent accidental contact with the cutter and also to press the tape being cut down upon the bead while the tape is being severed by the cutting blade.

It will thus be seen that rolled material may be pulled from the roll 2 and the end thereof brought downwardly to bring the material into contact with the top portion or ledge formed by the rolled bead 21. The cutter 24 may then be moved along its slot 23 through use of the handle 28 to sever that portion of the material which is disposed outside of the housing 10 from that which is attached to the roll 2. When the material comprising the rolled material 2 has an adhesive under surface such as is encountered in adhesive tape, the end thereof which is integral with the rolled material 2 will remain on the inner portion or ledge of the bead 21 in the manner illustrated in Fig. 2, thus permitting ready access to that material whenever it is desired to remove more from the roll 2. Furthermore with this type of tape, which is known to be difficult to cut, the adhesive side clings to bead 21, upon both sides of the slot 23 whereby the tape is in effect supported by the bead under tension thus greatly facilitating cutting of the tape.

Inasmuch as continued use of the cutter 24 tends to eventually dull the cutting edges 25 and 26 thereof we prefer to make provision for the removal of the cutter so that the cutting edges may be re-sharpened. This may be readily accomplished by cutting off one end 29 of the bead 21 in the manner illustrated in Fig. 1 so that the cutter 24 may be moved beyond the end of the slot 23 to permit bodily removal of the cutter 24, guiding cylinder 27 and handle 28 from the apparatus.

From the foregoing it will be observed that we have provided a holder and dispenser for rolled sheet material which may be manufactured in a neat and attractive form and that the apparatus is provided with a readily openable cover so that the rolled sheet material may be kept covered at all times and protected from dust, dirt, and the like.

It will be further observed that the device of our invention provides for the ready cutting of removed portions of said material from the roll on which it is contained and that the cutting portions of the cutting device are completely enclosed so that accidental injury to persons using the device is obviated.

It will be furthermore observed that the type of construction illustrated permits the ready removal of the rolls from the holder and ready insertion of new rolls of material thereinto and that the type of cutter mounting which is employed operates to hold the ends of rolls of adhesive material in such position that they may be readily grasped for the purpose of removing additional amounts of such material from the rolls.

While we have shown and described the preferred embodiment of our invention, we do not desire to be limited to any of the details of construction shown or described herein, except as defined in the appended claims.

We claim:

1. In a holder for rolled sheet material, the combination of: a roll supporting rod for removably receiving a roll of said sheet material; a tubular rail member having a longitudinally extending slot therein; bracket means extending transversely of said rail member at opposite ends thereof for supporting said rail member in substantially parallel relation to said rod; a guiding member slidably mounted in said tubular member; a cutter secured to said guiding member and extending through said slot, whereby movement of said cutter along said slot operates to cut said material unrolled from said roll and extended across said slot; and means for permitting removal of said cutter from said rail member comprising a notch in said tubular rail member intersecting said slot and having width and length dimensions sufficient to pass said guiding member.

2. In a holder for rolled sheet material, the combination of: a roll supporting rod for removably receiving a roll of said sheet material; a tubular rail member having a longitudinally extending slot therein; means mounting said rail member in substantially parallel relation to said rod; a guiding member slidably mounted in said tubular member; a cutter secured to said guiding member and extending through said slot, whereby a portion of said rolled material unrolled from said roll and extended across said slot may be cut from the remainder of said roll by moving said guiding member and cutter along said rail and across said material; handle means for so moving said cutter secured to the other end thereof and extending beyond said cutter; and wings extended laterally from each side of said handle and having under surfaces curved to lie in closely spaced parallelism to said tubular rail member, whereby said handle and wings serve to surround said cutter and prevent accidental injury thereon.

3. In a holder for rolled sheet material coated on one side with an adhesive composition, the combination of: a roll supporting rod for removably receiving a roll of said sheet material; a tubular rail member having a longitudinally extending slot therein; means mounting said rail member in substantially parallel relation to said rod; a guiding member slidably mounted in said tubular member; a cutter secured to said guiding member and extending through said slot, whereby a portion of said rolled material unrolled from said roll and extended across said slot with the adhesively coated side facing said rail member may be cut from the remainder of said roll by moving said guiding member and cutter along said rail and across said material; and means carried by the upper end of said cutter for pressing said material into contact with said rail as said cutter is moved therealong, whereby the severed portion of said material is temporarily adhesively fixed to the rail member at one side of said slot and whereby the end of said roll of material adheres to said rail member at the other side of said slot.

4. In a holder for rolled pressure-sensitive adhesive tape, the combination of: a substantially cylindrical sheet material housing having an open portion extending substantially the full length thereof; an arcuate cover member mounted for pivotal movement for closing said opening; end walls closing the ends of said housing; a removable roll supporting means mounted within said housing for supporting a roll of material therein; a substantially tubular rail positioned at and along the lower edge of the opening and immediately adjacent said housing, said tubular rail having a slot extending substantially the full length thereof; and cutting means mounted for movement in said slot and arranged to cut material extending thereacross, and adhering to said rail upon each side of said slot, said cutting means having a guiding member within said tubular rail and a handle without said rail for moving said cutting means throughout substantially the full length of said slot.

5. In a holder for rolled pressure-sensitive adhesive tape, the combination of: a substantially closed housing having an unobstructed interior of a size and shape to receive rolls of pressure-sensitive adhesive tape, said housing having a longitudinal opening extending substantially the full length of the housing, a movable cover for closing said longitudinal opening, a removable supporting means for supporting rolls of pressure-sensitive adhesive tape; and a tubular edge member on the housing and defining one longitudinal edge of said opening and providing a narrow ledge portion to which the adhesive tape will adhere and also having a slot extending substantially throughout its length immediately adjacent said ledge, said housing, removable supporting means, and tubular edge member being so related that a roll of adhesive tape having a radius equal to the distance from the roll support to said tubular member can be placed on said support and received in said housing; and cutting means mounted for movement along said tubular edge member to cut material extending across and adhering to said ledge, said cutting means comprising a guiding member within said tubular edge member, a handle means without said edge member, and a cutter secured to said handle and to said guiding member and operating through said slot.

6. In a holder and dispenser for rolled pressure-sensitive adhesive tape, the combination of: a substantially closed housing having an unobstructed interior of a size and shape to receive rolls of pressure-sensitive adhesive tape, said housing having a longitudinal opening extending substantially the full length of the housing, a movable cover for closing said longitudinal opening, a removable supporting means for supporting rolls of pressure-sensitive adhesive tape; and a cutter guide adjacent one longitudinal edge of said opening and providing a narrow ledge portion to which the adhesive tape will adhere in position to permit ready removal and also having a slot extending substantially throughout its length and dividing said ledge, said housing, removable supporting means, and cutter guide being so related that a roll of adhesive tape having a radius substantially equal to the distance from the roll support to said cutter guide can be placed on said support and received in said housing through said opening; and a cutting means mounted for movement along said cutter guide to cut adhesive tape extending across and adhering to said divided ledge, said cutting means comprising a guiding member engaging said cutter guide, a handle means extending beyond said cutter guide, and a cutter operable by said handle and guided by said cutter guide and operating through said slot.

7. In a holder and dispenser for rolled pressure-sensitive adhesive tape, the combination of: a substantially closed housing having an unobstructed interior of a size and shape to receive rolls of pressure-sensitive adhesive tape, said housing having a longitudinal opening extending substantially the full length of the housing, a movable cover for closing said longitudinal opening, a removable supporting means for supporting rolls of pressure-sensitive adhesive tape; and a cutter guide adjacent one longitudinal edge of said opening and providing a narrow ledge portion to which the adhesive tape will adhere and also having a slot extending substantially throughout its length and dividing said ledge, said housing, removable supporting means, and cutter guide being so related that a roll of adhesive tape having a radius substantially equal to the distance from the roll support to said cutter guide can be placed on said support and received in said housing through said opening; and cutting means mounted for movement along said cutter guide to cut adhesive tape extending across and adhering to said divided ledge, said cutting means comprising a guiding member engaging said cutter guide, a handle means extending beyond said cutter guide, means for retaining the tape in contact with said ledge, and a cutter operable by said handle and guided by said cutter guide and operating through said slot.

8. The method of dispensing adhesive tape in roll form which comprises supporting the roll rotatably so that tape may be pulled therefrom, pulling the tape and securing that portion thereof which is to be severed to fixed parts slightly separated from each other by moving the held portion laterally and utilizing the adhesive material carried by the tape for securement, and then severing the tape between the points of securement by moving a cutting element laterally against the tape from one edge portion in the direction of the other edge portion.

9. The method of dispensing adhesive tape in roll form to provide a severed piece of the desired length, which comprises partially unwinding the roll, pressing that portion of the tape which is to be severed against closely spaced points of securement using for securement the adhesive material carried by the tape, and then cutting the tape between the points of securement, utilizing the space between the points of securement as a guideway for guiding the cutting instrument.

10. The method of dispensing surgical plaster from a roll in a measured length, which comprises drawing off a length of the plaster, pressing a portion of said length into adhesive engagement with a guideway at opposite sides of the latter so that it is adhesively connected to the guideway, and then running a knife along the guideway to sever the plaster between its points of securement.

11. A dispensing device for adhesive tape in roll form, comprising a mounting for a roll, a guide arranged transversely to the tape issuing from the roll and presenting spaced points in close proximity to each other lengthwise of the tape and to which the tape is secured by its adhesive material while being cut, a knife mounted to cut the tape between the points of securement, and a member connected to and operating in advance of the knife to press the tape material against the guide.

12. A dispensing device for adhesive tape, comprising a mounting having a base member and a pair of brackets supported thereby in spaced-apart relation, a shaft member removably mounted in and extending between said brackets, a plurality of rolls of wound adhesive tape arranged side by side on said shaft and having depending end portions of tape in a forward accessible position at the front of the device, a guideway in fixed relation to the mounting having elongated, narrow portions spaced apart at a slight interval and spaced from the axes of the rolls behind the depending tape ends and furnished with rounded front surfaces providing spaced points of securement to which each tape end is secured by its adhesive material, and a cutting knife for the tape extending into and guided along said guideway.

ALEXANDER C. GILLANDERS.
HARRY H. DAGGETT.